United States Patent [19]

Kumar

[11] Patent Number: 4,814,089

[45] Date of Patent: Mar. 21, 1989

[54] CHROMATOGRAPHIC SEPARATION METHOD AND ASSOCIATED APPARATUS

[75] Inventor: M. Lalith Kumar, Pittsburgh, Pa.

[73] Assignee: Suprex Corporation, Pittsburgh, Pa.

[21] Appl. No.: 157,020

[22] Filed: Feb. 17, 1988

[51] Int. Cl.$^4$ ............................................. B01D 15/08
[52] U.S. Cl. ........................................ 210/659; 55/67; 436/161
[58] Field of Search ............... 210/635, 656, 659, 137, 210/198.2; 55/67, 197, 386; 422/70; 436/161, 162

[56] References Cited

U.S. PATENT DOCUMENTS

| | | | |
|---|---|---|---|
| 3,250,057 | 5/1966 | Clarke | 55/67 |
| 3,646,950 | 3/1972 | Takehisa et al. | 137/13 |
| 3,790,348 | 2/1974 | Bossart et al. | 23/254 EF |
| 4,073,725 | 2/1978 | Silverman | 210/659 |
| 4,083,702 | 4/1978 | Hartigan et al. | 55/67 |
| 4,124,358 | 11/1978 | Muller | 55/67 |
| 4,479,380 | 10/1984 | Novotny et al. | 73/61.1 C |

OTHER PUBLICATIONS

Giddings et al, Dense-Gas Chromatography at Pressures up to 2000 Atmospheres, Jour. of Chromatographic Science (May 1969).
Jentoft et al., Pressure-Programmed Supercritical Fluid Chromatography of Wide Molecular Weight Range Mixtures, Jour. of Chromatographic Science, p. 138, Mar. 1970.
Novotny et al., Temperature and Pressure Effects in Supercritical Fluid Chromatography, Jour. of Chromatographic Science, p. 17, Jun. 1971.
Hartman, Fluid Chromatography of Styrene Oligomeres, Doctural Dissertation at Albert-Ludwig University, Jun. 1977.
J. E. Conaway et al., J. Chromatogr. Sci. 16, Mar. 1978.
P. A. Peaden et al., Anal. Chem 52, No. 14, Dec. 1980, pp. 2268–2271.
Jorgenson et al., New Techniques for Liquid Chrom. in Open-Tubular Columns, Journal of Pharmaceutical & Biomedical Analysis, vol. 2, No. 2, pp. 191–196 (1984).
Grob, Modern Practice of Gas Chromatography, 2nd Edition, John Wiley & Sons, Jun. 1985, pp. 1–6.
Richter et al., Modified Flame Ionization Detector for Analysis of Large Molecular Weight Polar Compounds by Capillary Supercritical Fluid Chrom., Jour. of High Resolution Chrom. & Chrom. Communications, Jun. 1985, pp 297–300.
Smith et al., Performance of Capillary Restrictors in Supercritical Fluid Chromatography, Analytical Chemistry, pp. 2057–2064, Aug. 1986.
Hirata et al., Control of Flow Rate in Supercritical Fluid Chromatography, p. 627, Chromatography, vol. 21, No. 11 (1986).

*Primary Examiner*—Ernest G. Therkorn
*Attorney, Agent, or Firm*—Arnold B. Silverman

[57] ABSTRACT

In one embodiment of the invention supercritical fluid chromatographic separation may be accomplished by apparatus which includes a column, an oven for maintaining the temperature of a sample in the oven, an injector for delivering a sample containing fluid to the column and a pump for delivering carrier fluid to the injector. A discharge outlet for receiving processed fluid from the column contains one or two restrictors and a nozzle for discharge of processed fluid. The pump also delivers fluid which is the carrier fluid not containing the sample to a position in the pressure control inlet so as to alter the linear velocity of the sample containing fluid through the column. A controller controls operation of the oven and pump. A valve and a transducer may be positioned in the line between the pump and the discharge outlet in order to permit adjustment of the pressure of the unprocessed carrier fluid being introduced into the discharge outlet by the controller. The method of this embodiment may employ equipment of this type to effect chromatographic separation at the desired flow rate.

19 Claims, 3 Drawing Sheets

CHROMATOGRAPHIC SEPARATION METHOD AND ASSOCIATED APPARATUS

BACKGROUND OF THE INVENTION

1. Field Of The Invention

The present invention relates to apparatus and associated method for the chromatographic separation of materials and, more specifically, it focuses primarily upon supercritical fluid chromatographic separation.

2. Description Of The Prior Art

It has long been known to employ chromatography as a means for separating constituents from a sample and evaluating the same. Generally, a sample is introduced into a packed or open tubular column in a mobile phase which is adapted to interact with the materials contained in the column in order to effect a separation which may be analyzed by a detector positioned at the outlet end of the column.

It has been known to employ gas chromatography, liquid chromatography and supercritical fluid chromatography which is sometimes known as dense gas chromatography. See, generally, Grob, Modern Practice of Gas Chromatography, 2nd Edition, John Wiley & Sons (1985); Jorgenson et al., New Techniques for Liquid Chromatography in Open-Tubular Columns, Journal of Pharmaceutical & Biomedical Analysis, Vol. 2, No. 2, pages 191-196, (1984) and U.S. Pat. No. 4,479,380.

It has also been known to employ capillary columns in various types of chromatography including packed and unpacked column supercritical fluid chromatography, Hartmann, Fluid Chromatography of Styrene Oligomeres (1977) and U.S. Pat. No. 4,479,380. See also, U.S. Pat. No. 4,124,358.

It has been known in connection with chromatography to employ flame detectors. See generally, U.S. Pat. No. 3,790,348. Many types of detectors employed with supercritical fluid chromatography such as flame ionization detectors, nitrogen-phosphorous detectors, and flame photometric detectors operate at or near atmospheric conditions, while other detectors such as mass spectrometric operate at less than atmospheric conditions. As a result, it becomes desirable in supercritical fluid chromatography to reduce the pressure of the column effluent to atmospheric pressure. Highly sensitive detection of substances separated in the chromatograph have been detected by flame detectors. This is accomplished by ionizing the column effluent in a detector chamber. The chamber consists of an air/hydrogen flame and two electrodes, one above and one below the flame. The electrode above the flame collects the resulting electrons and amplifies the ionization current generated for delivery to the input of an electrometer amplifier.

Various aspects of the column-detector interface have been recognized. It has been known that problems are associated with depressurization and solvent cluster formation. Giddings et al., Dense-Gas Chromatography at Pressures up to 2000 Atmospheres, Jour. of Chromatographic Science (1969); Jentoft et al., Pressure-Programmed Supercritical Fluid Chromatography of Wide Molecular Weight Range Mixtures, Jour. of Chromatographic Science, p. 138 (1970). It has been known to attempt to employ pinched platinum irridium tubing, Smith et al., Performance of Capillary Restrictors in Supercritical Fluid Chromatography, Analytical Chemistry (1986), pin holes in disks and straight walled capillary restrictors, U.S. Pat. No. 4,479,380. It has also been known to use tapered restrictors, large interface heating zones and increasing the pressure drop by coating the capillary tubing with a polymer, Richter et al., Modified Flame Ionization Detector for Analysis of Large Molecular Weight Polar Compounds by Capillary Supercritical Fluid Chromatography, Jour. of High Resolution Chromatography & Chromatography Communications (1985). These prior art disclosures were directed toward achieving smoother depressurization and the ability to heat the depressurized stream better. This was accomplished by employing thin walled capillary tubing or using tapered capillary tubing and/or using additional heating zones to facilitate better heat transfer properties to carbon dioxide. Various forms of fittings have been known in chromatography. See, for example, U.S. Pat. No. 4,083,702.

In spite of these known flame detector disclosures, here remains a significant problem in that the solution of the substances in the carrier gas tends to become unstable through the expansion and substances conglomerate to flocculate or other aggregates which can become so large that a visible veil may appear. With higher substance concentration, condensation may occur. The undesired result of such action is that the peaks are distorted with jagged spikes. These distortions are attributable to the bursting of the previously flocculated substance particles in the flame. This renders the reproduction of the measurement difficult if not impossible.

It has been suggested to operate the flame ionization detector at the pressure of the separating column, but this is not practical as the control of the fuel gases and of the flame becomes much too complicated. Decreasing of column pressure prior to introduction into the flame ionization detector has tended to result in undesirable flocculation. In order to achieve desired smooth depressurization, solutes that do precipitate are swept through into the detector. The mobile phase should not be allowed to condense before detection as this would result in ion bursts that would produce extra electronic signals in the detector. Another problem with high pressure fluid depressurization is that it reduces the temperature of the fluid and flame. In some cases such as with carbon dioxide, the expansion of the fluid may actually lead to a two phase region. Formation of liquid or solid phases could lead to sudden expansions in the flame leading to spikes in the signal and instability of the flocculant resulting in spike output. Further, variation in the flame temperature introduces noise in the baseline of the output.

It has been known to modify the fluid flow rate by controlling the pressure drop through introduction of a backpressure into the fluid flow upstream of the nozzle. See P. A. Peaden, et al., Anal. Chem. 54, 1090-1093 (1982). The column in the oven is connected to a restrictor and the pressure downstream of the restrictor and upstream of the nozzle is maintained in any desired pressure which is typically slightly above the critical pressure through the introduction of very high pressure nitrogen. The maximum pressure nitrogen was limited to 1500 psia. This maximum is quite low and would limit the range of flow and therefore was not widely used.

It has not been known to control simultaneously pressure and flow programming capability with a wide range of flow in supercritical fluid chromatography. As a result, certain analysis are not attainable with the known means.

Flow control in gas chromatography through progressive increasing in pressures and mixing of effluent gas has been suggested. See U.S. Pat. No. 3,250,057.

It has been known to employ pressure programming in supercritical chromatography. See, Novotny et al., Temperature and Pressure effects in Supercritical Fluid Chromatography, Jour. of Chromatographic Science, p. 17 (1971). See also, U.S. Pat. No. 3,646,950 which, while not relating to chromatography, suggests pressure alterations to control fluid flow rates.

It has been known in supercritical fluid chromatography to maintain the flow rate constant during pressure programming by employing two pumps, one of which delivers makeup flow to maintain backpressure. Associated restrictors are employed. See Hirata et al., Control of Flow Rate in Supercritical Fluid Chromatography, p. 627, Chromatography, Vol. 21, No. 11 (1986). This approach requires the use of two pumps, manual coordination therebetween and does not employ information feedback in effecting control. See also U.S. Pat. No. 4,479,380 which discloses the use of two gas tanks in open-tubular supercritical chromatography.

A fluid with its temperature and pressure near the critical points is known as a supercritical fluid. Under such conditions, the density of the fluid is similar to that of a liquid, but the mass transfer properties are in between those of liquids and gases. The diffusion coefficient of the solute in the supercritical fluid is on the order of twice the magnitude of those in liquids.

In chromatography it is often necessary to control the flow of the fluid as well as the pressure. This is particularly true in supercritical fluid chromatography.

Controlling the density of a supercritical fluid by pressure programming has been known. See R. E. Jentoft et al., Journal in J. Chromatogr. Sci. 8, 1970, pages 138-142; J. E. Conaway et al., J. Chromatogr. Sci. 16, 1978, pages 102-110; and U.S. Pat. No. 4,479,380.

Temperature programming has been used in gas chromatography to change the solute retention time in the column. Flow programming has been used in liquid chromatography and has some relationship conceptually to the temperature programming in gas chromatography. It has also been known to use flow programming in packed supercritical fluid chromatography, but it has not been believed to have been used in capillary supercritical fluid chromatography.

In spite of the systems known to the prior art, there remains a very real and substantial need for an improved system for use in supercritical fluid chromatography to a more efficiently separate solute with a high degree of resolution.

SUMMARY OF THE INVENTION

The present invention has met the above-described need by providing means for effectively controlling the flow rate through a column such as a capillary or packed column in supercritical fluid chromatography without requiring replacement of a restrictor. This is accomplished by simultaneous flow and pressure programming. A high pressure pump provides a fluid to an injector which in turn introduces a sample into the fluid and delivers the fluid containing sample to a column which is positioned inside an oven which serves to maintain the fluid sample at the desired temperature. A flowmeter may be interposed between the pump and injector in order to monitor the flow rate. A portion of the fluid sample separates as it passes through the column after which the fluid passes through a first restrictor. The high pressure pump has a second outlet for delivering the fludd (without sample) to a pressure control inlet which is positioned between the first restrictor and the nozzle. By adjusting the pressure of the fluid introduced at the pressure control inlet, the flow rate of the fluid sample through the column may be controlled.

A second restrictor may be interposed between the pressure control inlet and the nozzle in order to provide a further flow control. Detector means may be positioned so as to receive fluid emerging from the second restrictor in order to analyze the same.

A control valve, which may be controlled by any suitable means, is adjustable in order to control the pressure of the fluid entering the pressure control inlet. A transducer may also be provided so as to monitor the pressure of the fluid exiting the control valve and to thereby provide feedback information to the controller to permit further adjustments.

Where the detector means is a flame detector, it may be advantageous to increase the temperature of the auxiliary fluid such that it compensates for reduction in temperature of the column effluent fluid as it emerges from the column. This results in the desired reduction in pressure before entry into the flame detector while avoiding the hereinbefore discussed problems. This may be accomplished readily by employing heat generating means in order to control the fluid entering the pressure control inlet. The operation of the heat generating means is suitably coordinated with control means.

It is an object of the present invention to provide an automated method for supercritical fluid chromatography and associated apparatus which separates solute efficiently and with high resolution.

It is a further object of the invention to provide such a system which effects precise flow rate control and adjustment without requiring replacement of restrictors.

It is a further object of the present invention to provide such a system wherein smooth depressurization of the column effluent is achieved so as to increase the efficiency of operation of the flame detector and resist spikes in the chromatograph resulting from undesired solidification or agglomeration.

It is a further object of this invention to provide such a system which while maintaining temperature of the fluid sample substantially constant varies pressure downstream of the column by means of a separate fluid flow which controls pressure of flow through the column and thereby controls flow rate.

It is a further object of this invention to provide such a system which facilitates reduction in the time required for analysis by varying the flow rate.

It is a further object of the invention to provide such a system which may be employed with open tubular or packed column supercritical chromatography.

It is another object of this invention to provide such a system which permits simultaneous flow and pressure (or density) programming.

It is yet another object of the invention to provide such a system wherein the temperature of the fluid in the first restrictor may be controlled through control of the temperature in the auxiliary flow.

These and other objects of the invention will be more fully understood from the following description of the invention on reference to the illustrations appended hereto.

DESCRIPTION OF THE PREFERRED EMBODIMENTS

In effecting supercritical chromatographic separation it is frequently necessary to effect flow control as well as temperature and pressure control. As a solute's solubility depends on the density of the fluid, controlling the pressure can be useful in separating the solutes efficiently and with high resolution.

In existing supercritical fluid chromatography, the efficiency and retention time is limited by the fluid flow rate. The fluid flow rate is controlled by using a restrictor which typically is a tube of a particular diameter which corresponds with a fixed pressure drop. For a given pressure the flow rate cannot be altered without changing the restrictor to one of a different diameter. Unfortuntely, in supercritical fluid chromatography it is often necessary to increase or decrease the flow or even keep it constant under varying pressure in a single analysis and the opportunity for changing restrictors is not presented.

While flow programming has been used in packed column supercritical fluid chromatography, it has not been used in capillary supercritical fluid chromatography. Simultaneous flow and pressure programming has not been employed for both packed and capillary column supercritical fluid chromatography.

Figure 1:
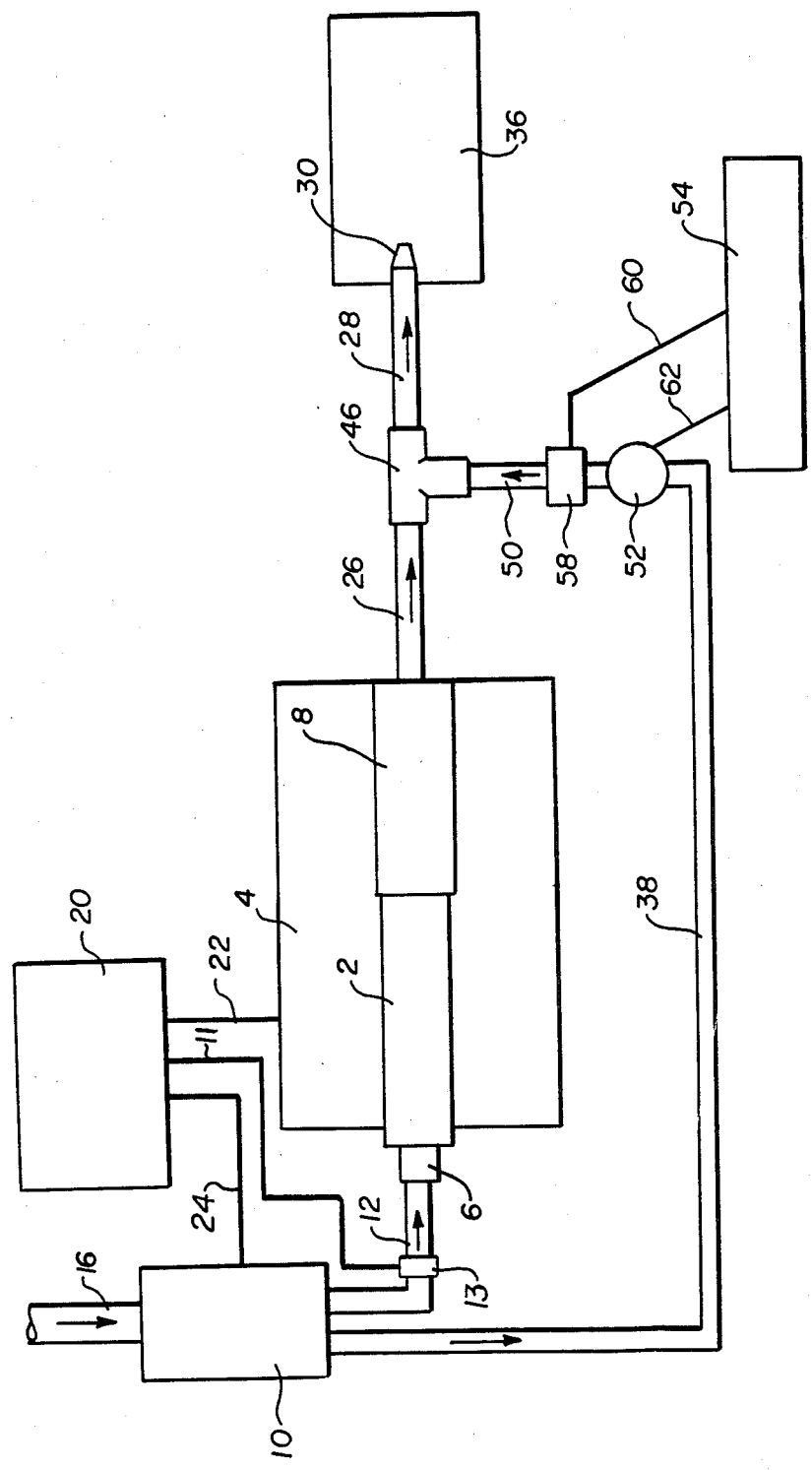
FIG. 1 is a schematic illustration of a form of apparatus employed in the present invention for supercritical fluid chromatography pressure and flow rate control.

Referring now specifically to FIG. 1, there is shown a column 2 which may be a capillary column. The column 2 disposed within oven 4 which serves to maintain the desired temperature. An injector 6 receives a carrier fluid from pump 10 through first conduit means 12, introduces the sample therein and delivers the fluid containing sample to column 2. The pump 10 receives a supply of carrier fluid through pump inlet 16. The sample may be introduced into the injector 6 by any conventional means.

The carrier fluid passes through flowmeter 3 which monitors flow rate of the carrier fluid and is connected to controller 20 by lead 11. The carrier fluid passes through first conduit 12, picks up the sample in injector 6 and delivers it to column 2 Controller 20 has lines 22 and 24 connected, respectively, to the oven 4 and pump 10 in order to control the same. The processed fluid sample exits column 2 through a discharge outlet which, in the form shown, contains a union 8 in communication with both column 2 and a downstream first restrictor 26. A second restrictor 28 is adapted to receive processed fluid from first restrictor 26. The restrictor 28 has a discharge opening 30 which in the form shown is a nozzle. Opening 30 could, in lieu of being a nozzle, be provided in other forms. It could, for example, be provided with a frit of the ceramic or polymer type, for example. In the form shown, detector means 36 receives the processed fluid from second restrictor 28 and analyzes the same.

In order to provide enhanced flow rate adjustability for this system, a second fluid flow path which may be controlled in respect of pressure and temperature is provided. Second conduit means 38 receives a fluid, which is the same carrier fluid, from another outlet of the pump 10. This fluid is also introduced into the pump 10 through inlet 16. A tee 46 provides a mixing area and sealed connection between the outlet of first restrictor 26 and the outlet of second conduit means 38 where it enters the tee 46 and thereby facilitates intermixture of the processed fluid passing out of column 2 and the auxiliary fluid passing from the pump 10 through second conduit means 38 to the tee 46. The portion of the second conduit means 38 entering tee 46 will be referred to as portion 50 and may be considered as entering at a pressure control inlet, which in the form shown is a tee 46.

In a preferred embodiment of the invention, a control valve 52 is interposed in the second conduit means 38 intermediate the pump 10 and tee or pressure control inlet 46 in order to permit variations in the pressure in the auxiliary fluid. It will be appreciated that by adjusting the control valve 52, the pressure of the auxiliary fluid entering pressure control inlet 46 may be altered and thereby create a backpressure within column 2 so as to control the flow rate of the fluid sample within column 2.

It is preferred that the pump be a high pressure pump having a total output capacity of about 50 to 250 ml and pressures up to about 10,000 psia. The pressure of the auxiliary fluid in second conduit means 38 may assume a broad range of relationships with respect to the pressure of the fluid sample in column 2. It generally will be capable of having a pressure of about 10 to 100 percent of the column fluid sample pressure.

In chromatography, the flow rate through a column is a function of the column diameter and the linear velocity of the sample through the column. The linear velocity is directly related to the time required for the solvent peak and sample peaks to emerge from the system. The present invention employs control over backpressure through the pressure control inlet 46 as well as other variables effecting the desired linear velocity and thereby control emergence of the solvent peak. The time required to emerge from the system is known as the retention time. By controlling retention time, the efficiency and selectivity of the separation can be enhanced.

In order to provide for enhanced performance of the system, it is preferred that a microprocessor 54 which may form a part of controller 20, if desired, control the position of control valve 52. A transducer 58 is preferably disposed in the second conduit means 38 intermediate the control valve 52 and the tee 46 so as to monitor pressure of the auxiliary fluid emerging from control valve 52. Line 60 provides feedback to the microprocessor 54 of the pressure. The microprocessor 54 may responsively, through line 62, effect a change in the position of control valve 52 in order to establish the desired flow rate within column 2. As the controller 20 and microprocessor 54 may be of any suitable type known to those skilled in the art, details need not be provided herein.

The desired flow rate can be established by providing a flowmeter 13 in first conduit means 12 intermediate pump 10 and injector 6. The output of flowmeter 13 is delivered by lead 11 to controller 20 in order to monitor and permit adjustment of linear velocity of the flow sample through column 2. This facilitates simultaneous flow and pressure (density) programming.

The temperature of the auxiliary fluid stream is preferably maintained at around or higher than the critical temperature of the fluid. It is preferred that the auxiliary stream have a temperature about 5 to 50 percent higher than the temperature of the processed fluid sample.

Figure 2:
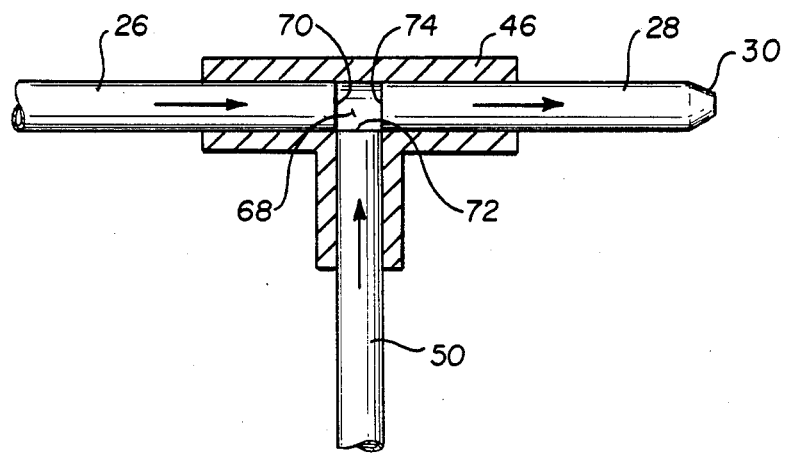
FIG. 2 is a schematic illustration of a form of connection between the principal discharge flow through a restrictor and the auxiliary flow conduit.

Referring to FIG. 2 details of a preferred form of mixing arrangement is shown. It will be seen that the pressure control inlet 46 provides a sealed chamber 68 into which extend the free or outlet end of first restrictor 26, the free or outlet end 72 of second conduit means portion 50 and the inlet end 74 of second restrictor 28. Flow being effected in the directions indicated by the arrows, the processed fluid sample emerging from first restrictor 26 will be admixed with the auxiliary fluid emerging from conduit 50 and will then pass into second restrictor 28. It will be appreciated that by controlling the pressure of the auxiliary fluid emerging from second conduit portion 50, the flow rate of the fluid sample through the column 2 may be controlled.

Figure 3:
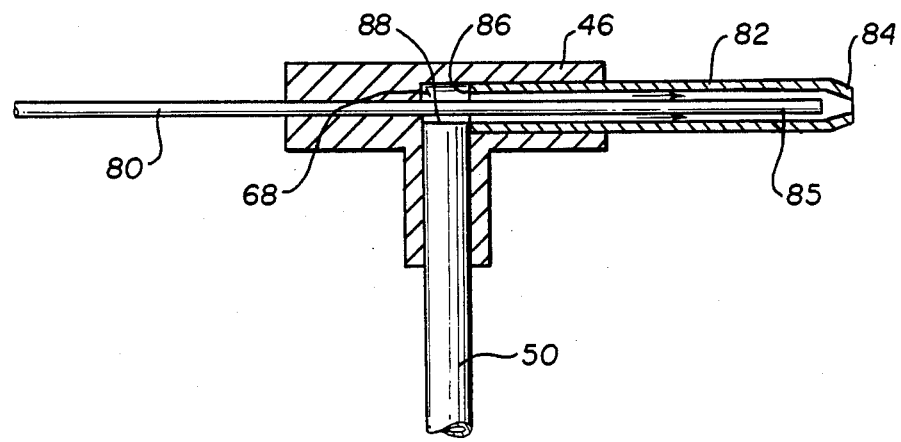
FIG. 3 is similar to FIG. 2, but shows a modified form of connection.

Referring to FIG. 3, an alternate embodiment of the invention will be considered. In this embodiment, the pressure control inlet or tee 46 has a sealed chamber 68 and receives auxiliary fluid through conduit sector 50 which has free end 88. The first restrictor 80, rather than having a discharge opening within the chamber 68, extends coaxially within the second restrictor 82 which has a discharge end 84. It will be appreciated that in operation auxiliary fluid emerging from discharge end 88 of conduit portion 50 will enter second restrictor 82 through entry opening 86 and will pass in the annulus between the exterior of first restrictor 80 and the interior of second restrictor 82 with mixing occurring adjacent the discharge end 85 of the first restrictor 80 after which discharge of the mixture is effected through the nozzle 84.

EXAMPLE

The pump 10 is preferably of the syringe or reciprocating type having a total output capacity of about 50 to 250 ml and an output pressure of up to about 10000 psia. Pump 10 has multiple outputs so that the carrier fluid may be delivered to both the injector 6 and the pressure control inlet 46. The same carrier fluid is employed in both channels.

A suitable pump is that sold under the trade designation SFC/200A Pump by Suprex Corporation of Pittsburgh, Pa.

The controller may take the form of any suitable controller which would be readily known to those skilled in the art and preferably is programmable in order to accomplish the objectives of the present invention. A suitable controller would be that sold under the trade designation of SFC/200A Controller sold by Suprex Corporation of Pittsburgh, Pa.

The control valve 52 is preferably a pressure regulating valve of the diaphragm type. A suitable valve is a pressure regulator type sold by Tescom of Minnesota. The flow rate of the fluid sample is a function of the pressure and viscosity and any changes in viscosity due to changes in temperature of the flow control module will affect the flow rate. The controller 20 will so establish temperature of the oven 4 so as to control the temperature of the fluid sample within column 2. The flow rate through the column 2 will be sufficiently slow as to facilitate effective temperature control and may, for example, be about 5 microliters/minute to about 10,000 microliters/minute.

It will be appreciated that by controlling pressure at pressure control inlet 46, the total fluid flow going into the detector 36 can be made substantially constant. This constant flow rate serves to reduce drift and electrical noise in the output of the detector 36. This serves to increase the sensitivity of the detector 36.

Figure 4:
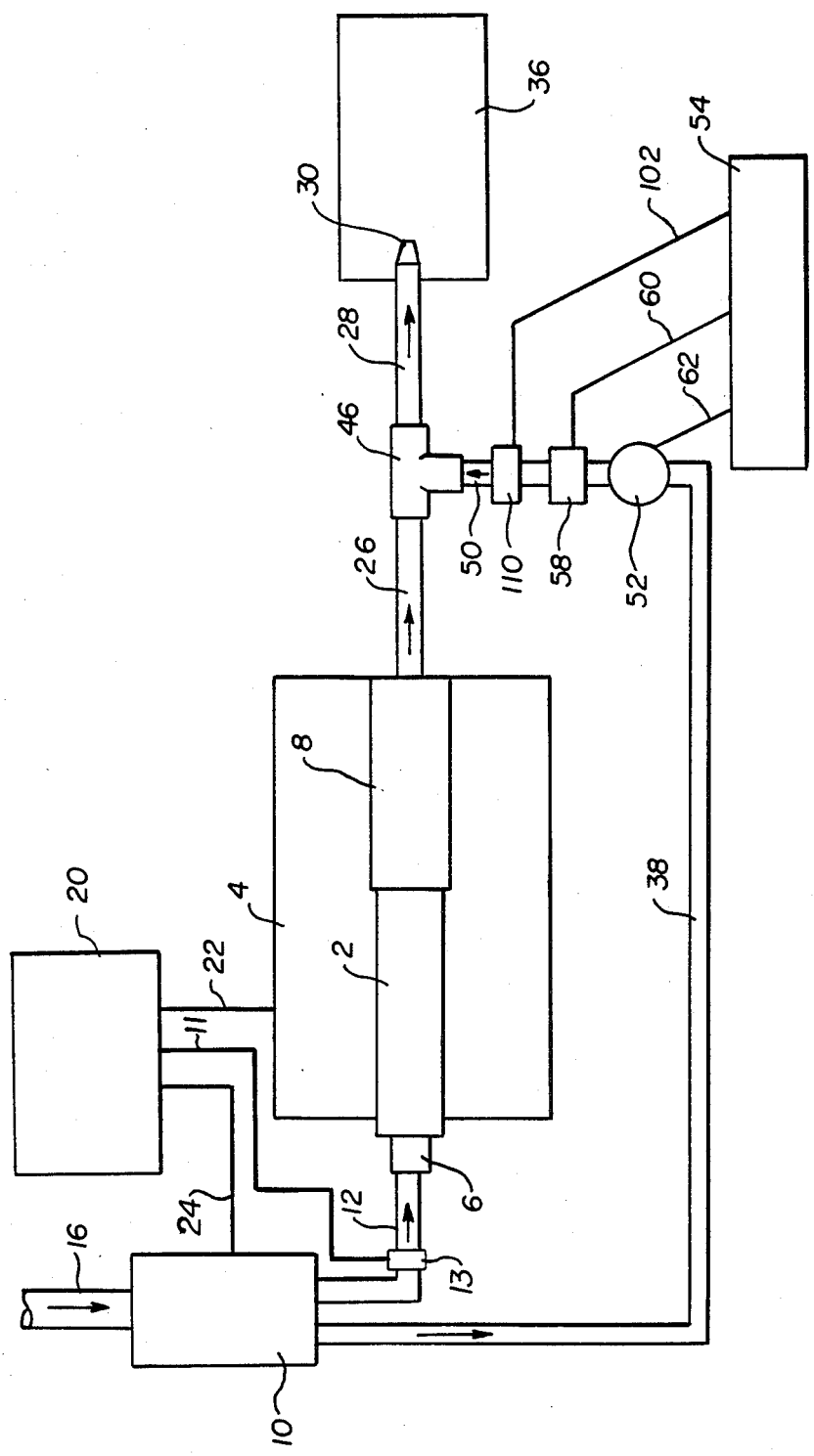
FIG. 4 is a schematic illustration of the form of apparatus similar to FIG. 1, but being modified so as to employ flame detector means and associated means for facilitating smooth pressure reduction of the column effluent.

Referring in greater detail to FIG. 4, there is shown apparatus generally similar to that of FIG. 1. In the second conduit means 38 there is provided heat generating means 110 which is operatively associated with microprocessor 54 through line 102. This heat generating means may take the form of a convective oven or an electrical heating element, for example. It is also preferably provided with a temperature sensing device (not shown) which may be of any conventional type. Such a device provides information to the microprocessor 54 regarding the temperature of the second fluid portion flowing through second conduit means 38.

In this embodiment of the invention, it is contemplated that as the pressure of the column effluent is reduced through expansion of the gas the temperature of that gas will drop. The auxiliary fluid which will enter into tee 46 will be maintained at such temperature as to compensate for the temperature loss of the effluent fluid and thereby provide a fluid at the desired temperature and pressure for effective analysis in the detector means 36 which, in this embodiment, may be a conventional flame detector.

The pressure of the column effluent in the region of the tee 46 may be maintained at any desired level such as about 50 to 500 atmospheres through the introduction of the auxiliary stream through conduit 50 in a manner hereinbefore described. The auxiliary stream is composed of the carrier fluid employed in the column. The pressure transducer 58 and control valve 52 serve to provide gas at the desired pressure within tee 46. It will be appreciated that as different gases have different critical pressures, the present system is readily adapted to compensate for this variable as well.

In general, in the preferred embodiment the auxiliarly fluid stream will be maintained at a temperature slightly higher than the temperature of the supercritical fluid. As the expansion of the column effluent fluid occurs the temperature reduces. In cases such as carbon dioxide the fluid may actually be in the two phase region after expansion. Introduction of the relatively high temperature auxiliary fluid upstream of the nozzle heats the low temperature partially expanded column effluent to a higher temperature such that expansion to atmospheric pressure would not result in the two phase region forming or otherwise adversely affecting the flame temperature.

It will be appreciated, therefore, that the apparatus of FIG. 4 and the associated method permit feeding of high molecular weight substances in a non-agglomerated state to the burner nozzle of the flame detector thereby avoiding numerous problems. This successful result is somewhat surprising in view of the extraordinary thermodynamic instability of the non volatile ioolated macromolecules in diluted gases wherein an immediate agglomeration of the macromolecules would normally be expected. The molecules, however, remain distributed in the arrangement according to the invention obviously in a metastable state even in the expanded column effluent gas without agglomeration until they enter the burner. This results in a smooth and stable process with the column effluent fluid expanding slowly from the column pressure to the auxiliary pressure. The introduction of the relatively high temperature auxiliary gas stream compensates for any temperature drop during the first stage expansion of the effluent fluid and further expansion to atmospheric pressure does not reduce the temperature in a meaningful manner. The substances do not flocculate upon expansion in either stage and the undesired jagged peaks in the chromatograph are resisted.

It will be appreciated that the two stage depressurization technique could be extended to any number of stages by cascading additional nozzles and introducing auxiliary pressures in sequence. Only one such stage is shown in FIG. 4, but one skilled in the art would readily understand that sequential tandem stages could be provided without great difficulty. In a multi-stage system each stage could be optimized in accordance with the depressurization sought to be achieved and the auxiliary fluid pressure at that stage.

It will be appreciated that the present invention contemplates a two stage controlled process wherein first restrictor 26 effects an initial reduction in pressure as restrictor 26 has a diameter which is about 2.5 to 100% of the diameter of column 2. Subsequently, introduction of the auxiliary pressurized fluid into tee 46 effects a second pressure reduction through establishing backpressure.

While for convenience of reference herein an automatically controlled valve 52 has been provided, it will be appreciated that if desired a manual control valve might be employed.

It will also be appreciated that by maintaining the pressure drop across the valve 52 constant the flow rate through the column 2 will remain constant and by varying the pressure drop, the flow rate can be varied. The value of the pressure drop will determine the flow rate of the supercritical fluid sample through the column 2.

It will be appreciated, therefore, that the present inventio has provided a method and apparatus for effecting improved efficiency, pressure and flow controlled, supercritical chromatography.

The value of the pressure drop will determine the linear velocity of the supercritical fluid through column 2 and thereby affect the retention time of the sample.

It will be appreciated that the present invention employs feedback regarding flow, temperatuae and pressure of the fluid portions to effect simultaneous control of linear velocity and pressure and thereby improves the results obtained.

Whereas particular embodiments of the invention have been described above for purposes of illustration, it will be evident to those skilled in the art that numerous variations of the details may be made without departing from the invention as defined in the appended claims.

I claim:

1. A method of effecting automated supercritical fluid chromatographic separation comprising
   providing a pump having inlet means and a first outlet in communication with an injector for introducing a fluid sample into a column disposed within an oven and a discharge passageway having a first restrictor and, a discharge outlet disposed downstream therefrom with automated controller means for controlling operation of said pump and said oven,
   said pump outlet means having means for delivering fluid to said discharge passageway at a pressure control inlet disposed intermediate said first restrictor and said discharge outlet,
   introducing a first portion of said fluid sample into said column by means of said injector,
   passing part of said first portion through said column under supercritical conditions and through said restrictor to said discharge outlet, and
   simultaneously with said first portion separation introducing a second fluid portion into said pressure control inlet at a predetermined pressure in order to control the flow rate of said first portion, whereby said pump will control the flow rate of said first portion of said sample fluid through said column under automated conditions.

2. The method of claim 1 including
   introducing as said second fluid sample portion a portion of said fluid.

3. The method of claim 2 including
   employing a capillary column as said column.

4. The method of claim 2 including
   employing a packed column as said column.

5. The method of claim 2 including
   providing flowmeter means intermediate said pump and said injector means, and
   monitoring the flow rate of said fluid to said injector by said flowmeter and employing information obtained in said monitoring to operate said process.

6. The method of claim 1 including
   providing said pump as a high pressure pump having a total output capacity of about 50 to 250 ml at 1000 psia.

7. The method of claim 1 including
   maintaining the temperature of said first fluid portion at or above its critical temperature.

8. The method of claim 7 including
   employing said oven to maintain the temperature of said first fluid portion at said temperature.

9. The method of claim 1 including
   employing said predetermined pressure in said second fluid portion to control sample retention time.

10. The method of claim 8 including
    providing a second restrictor intermediate said first restrictor and said discharge outlet, and
    introducing said second fluid portion at a pressure control inlet disposed between said first restrictor and said second restrictor.

11. The method of claim 10 including
    varying the sample fluid first portion flow rate through said column by varying said predetermined pressure of said second fluid portion.

12. The method of claim 11 including
    mixing the processed part of said first fluid portion which passes through said column and said second fluid portion at said pressure control inlet, and
    discharging said mixed portion through said discharge outlet.

13. The method of claim 12 including
    providing detector means operatively associated with said discharge outlet, and
    introducing said mixed portion into said detector means.

14. The method of claim 13 including
    employing an open tubular column as said column.

15. The method of claim 13 including
employing a packed column as said column.
16. The method of claim 13 including
providing a flame detector as said detector means, and
providing said second fluid portion of said fluid sample at an elevated temperature with respect to said processed part of said first fluid portion, whereby mixing of said two fluid portions will result in elevation of the temperature of said processed part of said first portion prior to introduction of said processed part of said first portion into said flame detector.
17. The method of claim 16 including
maintaining said fluid sample second portion at about 1 to 50% above the temperature of said processed portion of said first portion, whereby distortion of peaks in the resultant chromatograph will be resisted.
18. The method of claim 17 including
prior to mixing said processed part of said first fluid portion and said second fluid portion effecting an expansion of said processed part of said first fluid portion with a corresponding reduction in pressure and temperature therein.
19. The method of claim 18 including
effecting a reduction in the pressure of said processed part of said first fluid portion admixed with said second portion to approximately atmospheric pressure prior to introduction of said mixture into said flame detector.

* * * * *

UNITED STATES PATENT AND TRADEMARK OFFICE
CERTIFICATE OF CORRECTION

PATENT NO. : 4,814,089
DATED : March 21, 1989
INVENTOR(S) : M. LALITH KUMAR

It is certified that error appears in the above-identified patent and that said Letters Patent is hereby corrected as shown below:

Col. 2, line 18, "here" should be --there--.

Col. 4, line 2, "fludd" should be --fluid--.

Col. 5, line 54, "flowmeter 3" should be --flowmeter 13--.

Col. 5, line 58, a period --.-- should be inserted after "column 2".

Col. 8, line 46, "auxiliarly" should be --auxiliary--.

Col. 8, line 66, "ioolated" should be --isolated--.

Col. 9, line 44, "inventio" should be --invention--.

Claim 1, col. 9, line 68, the comma after "and" should be deleted.

Claim 6, col. 10, line 35, "1000" should be --10000--.

Signed and Sealed this

Seventh Day of November, 1989

Attest:

JEFFREY M. SAMUELS

*Attesting Officer*    *Acting Commissioner of Patents and Trademarks*